United States Patent
Liu et al.

(10) Patent No.: US 10,610,704 B2
(45) Date of Patent: Apr. 7, 2020

(54) BEAM SHAPING ASSEMBLY FOR NEUTRON CAPTURE THERAPY

(71) Applicant: NEUBORON MEDTECH LTD., Nanjing, Jiangsu (CN)

(72) Inventors: Yuan-Hao Liu, Jiangsu (CN); Pei-Yi Lee, Jiangsu (CN)

(73) Assignee: NEUBORON MEDTECH LTD., Nanjing, Jiangsu (CN)

( * ) Notice: Subject to any disclaimer, the term of this patent is extended or adjusted under 35 U.S.C. 154(b) by 0 days.

(21) Appl. No.: 16/143,949

(22) Filed: Sep. 27, 2018

(65) Prior Publication Data

US 2019/0022421 A1    Jan. 24, 2019

Related U.S. Application Data

(63) Continuation of application No. 15/825,690, filed on Nov. 29, 2017, now Pat. No. 10,124,192, which is a
(Continued)

(30) Foreign Application Priority Data

Dec. 8, 2014   (CN) .......................... 2014 1 0742679
Dec. 8, 2014   (CN) .......................... 2014 1 0743692
(Continued)

(51) Int. Cl.
*A61N 5/10*     (2006.01)
*G21K 1/10*    (2006.01)
(Continued)

(52) U.S. Cl.
CPC ............. *A61N 5/1077* (2013.01); *G21G 4/02* (2013.01); *G21K 1/10* (2013.01); *H05H 3/06* (2013.01);
(Continued)

(58) Field of Classification Search
None
See application file for complete search history.

(56) References Cited

U.S. PATENT DOCUMENTS 3,778,627 A    12/1973   Carpenter
4,599,515 A     7/1986   Whittemore
(Continued)

FOREIGN PATENT DOCUMENTS

CN     202802547 U     3/2013
EP       1895819 A1    3/2008
(Continued)

OTHER PUBLICATIONS

M. Adib et al. "On the use of bismuth as a neutron filter" Radiation Physics and Chemistry 66 (2003) 81-88. (Year: 2003).*
(Continued)

*Primary Examiner* — James Choi
(74) *Attorney, Agent, or Firm* — Locke Lord LLP; Tim Tingkang Xia, Esq.

(57) ABSTRACT

A beam shaping assembly for neutron capture therapy includes a beam inlet, a target having nuclear reaction with an incident proton beam from the beam inlet to produce neutrons forming a neutron beam defining a main axis, a moderator adjoining to the target, a reflector surrounding the moderator, a thermal neutron absorber adjoining to the moderator, a radiation shield arranged inside the beam shaping assembly and a beam outlet. The neutrons are moderated to epithermal neutron energies. The reflector leads the neutrons deviated from the main axis back, and a gap channel is arranged between the moderator and the reflector. The thermal neutron absorber is used for absorbing thermal neutrons so as to avoid overdosing in superficial normal tissue during therapy. The radiation shield is used for
(Continued)

shielding leaking neutrons and photons so as to reduce dose of the normal tissue not exposed to irradiation.

17 Claims, 4 Drawing Sheets

Related U.S. Application Data continuation of application No. 14/705,784, filed on May 6, 2015, now Pat. No. 9,889,320.

(30) Foreign Application Priority Data

Dec. 8, 2014 (CN) .................... 2014 2 0765213 U
Dec. 8, 2014 (CN) .................... 2014 2 0765424 U

(51) Int. Cl.
G21G 4/02 (2006.01)
H05H 6/00 (2006.01)
H05H 3/06 (2006.01)

(52) U.S. Cl.
CPC ......... *H05H 6/00* (2013.01); *A61N 2005/109* (2013.01); *A61N 2005/1094* (2013.01); *A61N 2005/1095* (2013.01)

(56) References Cited

U.S. PATENT DOCUMENTS

| | | | |
|---|---|---|---|
| 4,760,266 A | 7/1988 | Schulz | |
| 5,392,319 A * | 2/1995 | Eggers | H05H 3/06 376/151 |
| 5,703,918 A | 12/1997 | Hiismaki et al. | |
| 5,744,813 A | 4/1998 | Kumakhov | |
| 5,903,622 A | 5/1999 | Yoon et al. | |
| 2010/0061500 A1 | 3/2010 | Lou et al. | |
| 2010/0067640 A1 | 3/2010 | Willis et al. | |
| 2011/0158369 A1 * | 6/2011 | Larson | G21B 1/00 376/107 |
| 2012/0330084 A1 | 12/2012 | Pantell et al. | |
| 2014/0179978 A1 | 6/2014 | Pantell et al. | |
| 2016/0326062 A1 * | 11/2016 | Furuya | A61N 5/10 |

FOREIGN PATENT DOCUMENTS

| | | | |
|---|---|---|---|
| JP | H1157043 A | | 3/1999 |
| JP | 2007240330 A | | 9/2007 |
| JP | 2007242422 A | * | 9/2007 |
| JP | 2007242422 A | | 9/2007 |
| JP | 200822920 A | | 2/2008 |
| JP | 2013019692 A | | 1/2013 |
| JP | 2014115122 A | | 6/2014 |

OTHER PUBLICATIONS

Maucec, Marko, "Design of epithermal neutron beam for clinical BNCT treatment at Slovenian TRIGA research reactor" ENS RRFM '99. (Year: 1999).*
Meadows et. al. "The Thermal-Neutron-Absorption Cross Sections of 6Li and 10B" Nuclear Science and Engineering: 40, 12-16 (1970). (Year: 1970).*
Rasouli: F.S. Rasouli et al., "Design of a model for BSA to meet free beam parameters for BNCT based on multiplier system for D-T neutron source" 39 Annals of Nuclear Energy, pp. 18-25 (2012) (Year: 2012).*
Joshua P. Sroka, Design of a Moderator Assembly Delimiter for an ABNS for BNCT, The Monte Carlo Method: Versatility Unbounded in a Dynamic Computing World (Chattanooga, Tennessee, Apr. 17-21, 2005) (Year: 2005).*
China Patent Office, "Office Action", dated May 30, 2019, China.
Japan Patent Office, "Office Action", dated Jun. 18, 2019, Japan.
M. Adib et al., On the use of bismuth as a neutron filter, Radiation Physics and Chemistry, 2003, 81-88, 66.
Y. Kasesaz et al., Optimization of the beam shaping assembly in the D-D neutron generators-based BNCT using the response matrix method, Applied Radiation and Isotopes, 2013, 55-59, 82.
M. R. Eskaandari et al., Selecting the best proton energy in 7Li(p,n)7Be reaction use in BNCT, World Congress on Medical Physics and Biomedical Engineering, 2013, 1608-1612, 39.
Marko Maucec, Design of epithermal neutron beam for clinical BNCT treatment at Slovenian TRIGA research reactor, 1999.

* cited by examiner

BEAM SHAPING ASSEMBLY FOR NEUTRON CAPTURE THERAPY

RELATED APPLICATION INFORMATION

This application is a continuation of U.S. patent application Ser. No. 15/825,690, filed on Nov. 29, 2017, which is a continuation of U.S. patent application Ser. No. 14/705,784, filed on May 6, 2015, now U.S. Pat. No. 9,889,320 issued on Feb. 13, 2018, which claims priority to Chinese Patent Application No. CN 201410743692.9, filed on Dec. 8, 2014, CN 201420765424.2, filed on Dec. 8, 2014, CN 201410742679.1, filed on Dec. 8, 2014, and CN 201420765213.9, filed on Dec. 8, 2014, the disclosures of which are hereby incorporated by reference.

FIELD OF THE DISCLOSURE

The present disclosure relates generally to a beam shaping assembly, and, more particularly, to a beam shaping assembly for neutron capture therapy.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

BNCT takes advantage that the boron ($^{10}$B)-containing pharmaceuticals have high neutron capture cross section and produces $^4$He and $^7$Li heavy charged particles through $^{10}$B(n,α)$^7$Li neutron capture and nuclear fission reaction. As illustrated in FIGS. 1 and 2, a schematic drawing of BNCT and a nuclear reaction formula of $^{10}$B (n,α) $^7$Li neutron capture are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

BNCT is also well known for binary cancer therapy, for its effectiveness depending on the concentration of the boronated pharmaceuticals and the number of the thermal neutrons at the tumor site. Thus, besides development of the boronated pharmaceuticals, improvement of flux and quality of the neutron source plays a significant role in BNCT researches.

The statements in this section merely provide background information related to the present disclosure and may not constitute prior art.

SUMMARY

In order to improve flux and quality of the neutron source, an aspect of the present disclosure provides a beam shaping assembly for neutron capture therapy including: a beam inlet; a target, wherein the target has nuclear reaction with an incident proton beam from the beam inlet to produce neutrons, and wherein the neutrons form a neutron beam defining a main axis; a moderator adjoining to the target, wherein the neutrons are moderated by the moderator to epithermal neutron energies, the moderator includes a first side facing to the beam inlet and a second side facing away from the beam inlet; a reflector surrounding the moderator, wherein the reflector leads the neutrons deviated from the main axis back to enhance epithermal neutron beam intensity; a radiation shield arranged inside the beam shaping assembly, wherein the radiation shield is used for shielding leaking neutrons and photons so as to reduce dose of the normal tissue not exposed to irradiation; and a beam outlet, wherein the target is received into the moderator, the first side of the moderator contacts with the reflector.

Implementations of this aspect may include one or more of the following features.

The beam shaping assembly is further used for accelerator-based boron neutron capture therapy.

A proton beam is accelerated by means of an accelerator to overcome coulomb repulsion energy of a target atomic nucleus and generate nuclear reaction with the target to produce neutrons, and the target is made of a metal material.

An epithermal neutron energy range ranges from 0.5 eV to 40 keV, a thermal neutron energy range is below 0.5 eV, and a fast neutron energy range is above 40 keV, and the beam shaping assembly reduces the quantity of thermal neutrons and fast neutrons; and wherein the moderator is made of a material having a cross section for principally acting with fast neutrons but hardly acting with epithermal neutrons, the reflector is made of a material having a high neutron reflection ability.

More particularly, the moderator is made of at least one of $D_2O$, $AlF_3$, Fluental™, $CaF_2$, $Li_2CO_3$, $MgF_2$ and $Al_2O_3$.

More particularly, the reflector is made of at least one of Pb or Ni.

Furthermore, the beam shaping assembly further includes a thermal neutron absorber adjoining to the moderator, and wherein the thermal neutron absorber is used for absorbing thermal neutrons so as to avoid overdosing in superficial normal tissue during therapy.

More particularly, the thermal neutron absorber is made of a material having a cross section for acting with thermal neutrons, such as $^6$Li, and an air passage is arranged between the thermal neutron absorber and the beam outlet.

More particularly, the radiation shield includes a photon shield and a neutron shield.

Further, all of the beam inlet, the moderator and the beam outlet are extended along the main axis.

Further, an outer surface of the moderator includes a first single flat tapered section tapered in a first direction away from the beam outlet.

Further, an outer surface of the moderator includes a second single flat tapered section adjoining to the first single flat tapered section and tapered in a second direction toward the beam outlet.

The beam shaping assembly further includes a gap channel arranged between the moderator and the reflector and enclosed by the reflector, the moderator and the thermal neutron absorber, and wherein the gap channel allows neutron beams to pass for enhancing epithermal neutron beam intensity.

In another aspect of the present disclosure a beam shaping assembly for neutron capture therapy is provided for improving flux and quality of the neutron source. The beam shaping assembly includes a beam inlet; a target, wherein the target has nuclear reaction with an incident proton beam from the beam inlet to produce neutrons, and wherein the neutrons form a neutron beam defining a main axis; a moderator adjoining to the target, wherein the neutrons are moderated by the moderator to epithermal neutron energies, and wherein the moderator has a first trapezidal cross section facing to the beam inlet; a reflector surrounding the moderator, wherein the reflector leads the neutrons deviated from the main axis back to enhance epithermal neutron beam intensity; a radiation shield arranged inside the beam shaping assembly, wherein the radiation shield is used for shielding leaking neutrons and photons so as to reduce dose of the normal tissue not exposed to irradiation; and a beam outlet.

Further, the moderator has a second trapezidal cross section facing away from the beam inlet and adjoining to the first trapezidal cross section.

More particularly, all of the beam inlet, the moderator and the beam outlet are extended along the main axis.

The beam shaping assembly further includes a gap channel arranged between the moderator and the reflector and enclosed by the reflector, the moderator and the thermal neutron absorber, and wherein the gap channel allows neutron beams to pass for enhancing epithermal neutron beam intensity.

More particularly, the moderator includes a recess for receiving the target and at least a part of the beam inlet and the reflector includes a recess for receiving the other part of the beam inlet.

In yet another aspect of the present disclosure, a beam shaping assembly for neutron capture therapy is provided for improving flux and quality of the neutron source. The beam shaping assembly for neutron capture therapy includes a beam inlet; a target, wherein the target has nuclear reaction with an incident proton beam from the beam inlet to produce neutrons, and wherein the neutrons form a neutron beam defining a main axis; a moderator adjoining to the target, wherein the neutrons are moderated by the moderator to epithermal neutron energies, the moderator includes a first side facing to the beam inlet and a second side facing away from the beam inlet, and wherein the outer surface of the moderator includes a cylindrical section; a reflector surrounding the moderator, wherein the reflector leads the neutrons deviated from the main axis back to enhance epithermal neutron beam intensity; a radiation shield arranged inside the beam shaping assembly, wherein the radiation shield is used for shielding leaking neutrons and photons so as to reduce dose of the normal tissue not exposed to irradiation; and a beam outlet, wherein the target is received into the moderator, all of the beam inlet, the moderator and the beam outlet are extended along the main axis, a distance from the target to the beam outlet is closer than a distance from the first side to the beam outlet, and wherein the moderator comprises a recess for receiving the target and at least a part of the beam inlet and the reflector comprises a recess for receiving the other part of the beam inlet.

More particularly, the outer surface of the moderator includes a cylindrical section and a tapered section adjoining to the cylindrical section.

Further, an outer surface of the moderator includes a first single flat tapered section tapered in a first direction away from the beam outlet and a second single flat tapered section adjoining to the first single flat tapered section and tapered in a second direction toward the beam outlet.

The beam shaping assembly further includes a gap channel arranged between the moderator and the reflector, and wherein the gap channel allows neutron beams to pass for enhancing epithermal neutron beam intensity.

Further, the first side is protruded from the target along a direction from the main axis to the beam inlet and the second side is protruded from the target along a direction from the main axis to the beam outlet.

The term 'cylindrical' or 'cylindrical section' referred in the embodiment of the present disclosure is an element with the contour in a substantially unchanged trend from one side to the other side along the illustrated direction. One of contour lines may be a line segment, like a corresponding one of the cylinder, or may be a high-curvature arc approximate to the line segment, like a corresponding one of a sphere with high curvature. The integral surface of the contour may be continuously connected or not if the surface of the cylinder or the high-curvature sphere is provided with many protrusions and grooves.

The term 'tapered' or 'tapered section' referred in the embodiment of the present disclosure is an element with the contour in a tapering trend from one to the other side along the illustrated direction. One of contour lines may be a line segment, like a corresponding one of the cone, or may be an arc, like a corresponding one of the sphere, and the integral surface of the contour may be continuously connected or not if the surface of the cone shape or the spherical shape is provided with plenty of protrusions and grooves.

Further areas of applicability will become apparent from the description provided herein. It should be understood that the description and specific examples are intended for purposes of illustration only and are not intended to limit the scope of the present disclosure.

Figure 1:
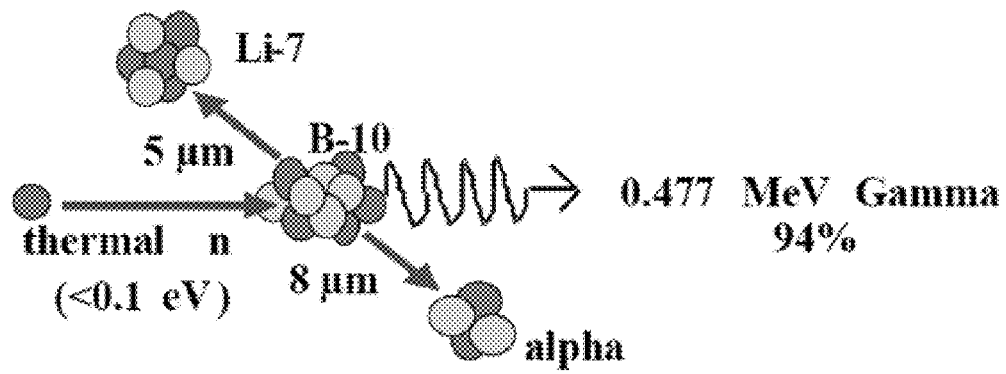
FIG. 1 is a schematic view of boron neutron capture reaction.
Figure 2:
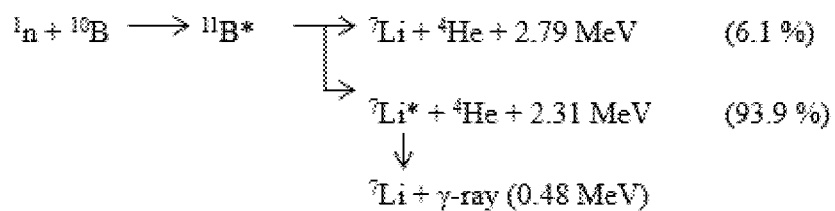
FIG. 2 is a nuclear reaction formula of $^{10}B$ $(n,\alpha)$ $^{7}Li$ neutron capture.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components comprise, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7$Li (p, n) $^7$Be and $^9$Be (p, n) $^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. The target in these embodiments of the present disclosure is made of lithium. However, well known by those skilled in the art, the target materials may be made of other metals besides the above-mentioned.

Requirements for the heat removal system differ as the selected nuclear reactions. $^7$Li (p, n) $^7$Be asks for more than $^9$Be (p, n) $^9$B does because of low melting point and poor thermal conductivity coefficient of the metal (lithium) target. In these embodiments of the present disclosure is $^7$Li (p, n) $^7$Be.

No matter BNCT neutron sources are from the nuclear reactor or the nuclear reactions between the accelerator charged particles and the target, only mixed radiation fields are produced, that is, beams comprise neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux>$1 \times 10^9$ n/cm$^2$s
Fast neutron contamination<$2 \times 10^{-13}$ Gy-cm$^2$/n
Photon contamination<$2 \times 10^{-13}$ Gy-cm$^2$/n
Thermal to epithermal neutron flux ratio<0.05
Epithermal neutron current to flux ratio>0.7

Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than $10^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons are considered as contamination. The dose exhibit positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than $2*10^{-13}$ Gy-cm$^2$/n.

3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than $2*10^{-13}$ Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

The prosthesis beam quality factors are deduced by virtue of the dose distribution in the tissue obtained by the prosthesis according to a dose-depth curve of the normal tissue and the tumors. The three parameters as follows may be used for comparing different neutron beam therapy effects.

1. Advantage Depth

Tumor dose is equal to the depth of the maximum dose of the normal tissue. Dose of the tumor cells at a position behind the depth is less than the maximum dose of the normal tissue, that is, boron neutron capture loses its advantages. The advantage depth indicates penetrability of neutron beams. Calculated in cm, the larger the advantage depth is, the larger the treatable tumor depth is.

2. Advantage Depth Dose Rate

The advantage depth dose rate is the tumor dose rate of the advantage depth and also equal to the maximum dose rate of the normal tissue. It may have effects on length of the therapy time as the total dose on the normal tissue is a factor capable of influencing the total dose given to the tumors. The higher it is, the shorter the irradiation time for giving a certain dose on the tumors is, calculated by cGy/mA-min.

3. Advantage Ratio

The average dose ratio received by the tumors and the normal tissue from the brain surface to the advantage depth is called as advantage ratio. The average ratio may be calculated using dose-depth curvilinear integral. The higher the advantage ratio is, the better the therapy effect of the neutron beams is.

To provide comparison reference to design of the beam shaping assembly, we also provide the following parameters for evaluating expression advantages and disadvantages of the neutron beams in the embodiments of the present disclosure except the air beam quality factors of IAEA and the abovementioned parameters.

1. Irradiation Time<=30 min (proton current for accelerator is 10 mA)
2. 30.0 RBE-Gy treatable depth>=7 cm
3. The maximum tumor dose>=60.0 RBE-Gy
4. The maximum dose of normal brain tissue<=12.5 RBE-Gy
5. The maximum skin dose<=11.0 RBE-Gy Note: RBE stands for relative biological effectiveness. Since photons and neutrons express different biological effectiveness, the dose above should be multiplied with RBE of different tissues to obtain equivalent dose.

Figure 3:
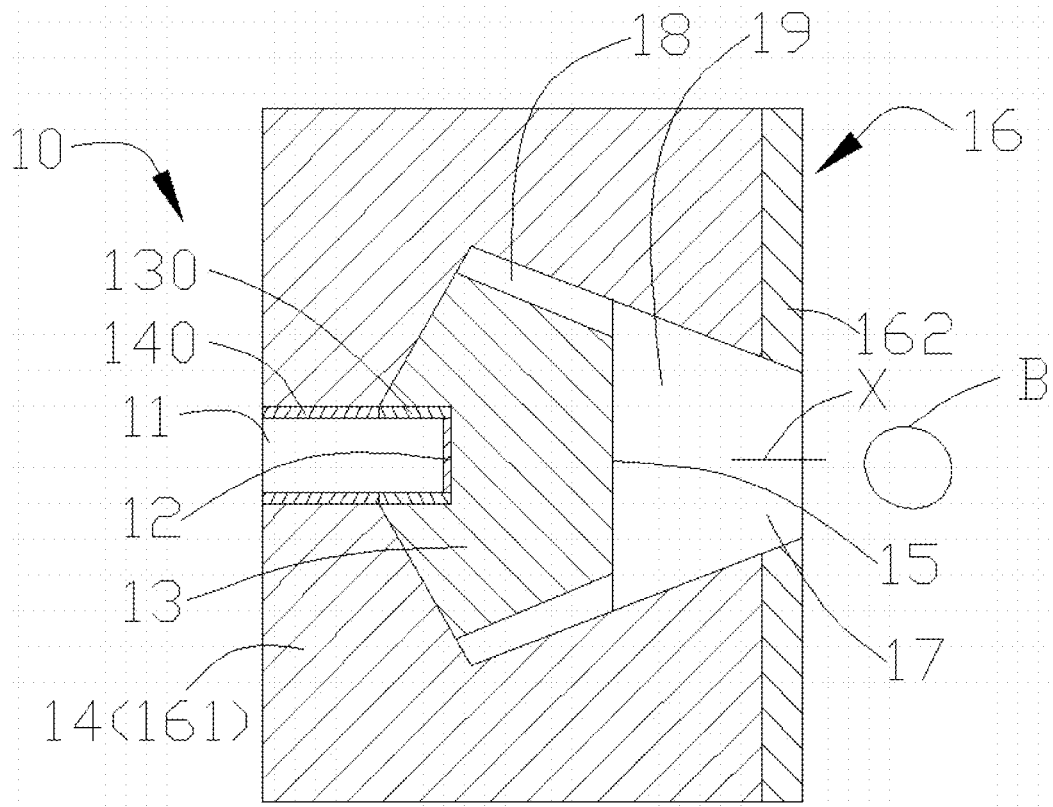
FIG. 3 is a schematic view of the beam shaping assembly for neutron capture therapy in the first embodiment of the present disclosure, wherein a gap channel is arranged between the moderator and the reflector.

In order to improve flux and quality of neutron sources, the embodiments of the present disclosure provides improvement of a beam shaping assembly for neutron capture therapy, preferably, improvement of a beam shaping assembly for AB-BNCT. As shown in FIG. 3, the beam shaping assembly 10 for neutron capture therapy in the first embodiment of the present disclosure comprises a beam inlet 11, a target 12, a moderator 13 adjacent to the target 12, a reflector 14 surrounding the moderator 13, a thermal neutron absorber 15 adjacent to the moderator 13, a radiation shield 16 and a beam outlet 17, wherein the radiation shield 16 is set inside the beam shaping assembly 10. The target 12 has nuclear reaction with an incident proton beam from the beam inlet 11 to produce neutrons; the neutrons form a neutron beam, the neutron beam defines a main axis X, and the neutrons are moderated by the moderator 13 to epithermal neutron energies, and the reflector 14 leads the neutrons deviated from the main axis X back to enhance epithermal neutron beam intensity; a gap channel 18 is placed between the moderator 13 and the reflector 14 so as to increase the epithermal neutron flux; the thermal neutron absorber 15 is used for absorbing thermal neutrons so as to avoid overdosing in superficial normal tissue during therapy; the radiation shield 16 is used for shielding the leaking neutrons and photons so as to reduce dose of a normal tissue not exposed to irradiation.

AB-BNCT accelerates a proton beam using an accelerator. Preferably, the target 12 is made of a metal material, and the proton beam is accelerated enough to overcome coulomb repulsion energy of a target atomic nucleus and has $^7$Li (p, n) $^7$Be reaction with the target 12 to produce neutrons. The beam shaping assembly 10 moderates the neutrons into epithermal neutron energies and reduces the quantity of thermal neutrons and fast neutrons; the moderator 13 is made of a material having a cross section for principally acting with fast neutrons but hardly acting with epithermal neutrons. Preferably, the moderator 13 is made of at least one of $D_2O$, $AlF_3$, Fluental™, $CaF_2$, $Li_2CO_3$, $MgF_2$ and $Al_2O_3$. The reflector 14 is made of a material having high neutron reflection ability, and is made of at least one of Pb or Ni preferably. The thermal neutron absorber 15 is made of a material having a cross section for acting with thermal neutrons and is made of $^6$Li preferably. An air passage 19 is placed between the thermal neutron absorber 15 and the beam outlet 17. The radiation shield 16 comprises a photon shield 161 and a neutron shield 162, and comprises a photon shield 161 made of lead (Pb) and a neutron shield 162 made of polyethylene (PE) preferably.

An outer surface of the moderator 13 includes the first tapered section and a second tapered section adjoining to the first tapered section, and a tapering direction of the first tapered section is opposite to a tapering direction of the second tapered section as shown in FIG. 3, the left side of the out surface of the moderator 13 is shaped in a first tapered section tapering gradually towards the left side, the right side of the out surface of the moderator 13 is shaped in a second tapered section tapering gradually towards the right side, and the two tapered sections connect to each other. Preferably, the left side of the out surface of the moderator 13 is shaped in a cone tapering towards the left side, and the right side may also be in other shapes adjacent to the cone, such as cylinder. The reflector 14 tightly surrounds the moderator 13, and a gap channel 18 is placed between the moderator 13 and the reflector 14. The moderator 13 includes a recess 130 for receiving the target 12 and at least a part of the beam inlet 11. The reflector 14 includes a recess 140 for receiving the other part of the beam inlet 11. The so-called gap channel 18 is an empty area unfilled by solid materials and allowing neutron beams to pass easily. The gap channel 18 may be an air or vacuum passage. The thermal neutron absorber 15 arranged in the immediate vicinity of the moderator 13 is made of a thin $^6$Li material layer, the photon shield 161 made of Pb in the radiation shield 16 may be integrated with or separated from the reflector 14, the neutron shield 162 made of PE in the radiation shield 16 may be arranged near the beam outlet 17. An air passage 19 is placed between the thermal neutron absorber 15 and the beam outlet 17, in this area, neutrons deviated from the main axis X may be kept leading back to enhance epithermal neutron beam intensity. A prosthesis B is arranged at a position about 1 cm away from the beam outlet 17. Well known by those skilled in the art, the photon shield 161 may be made of other materials for shielding photons; the neutron shield 162 also may be made of other materials or arranged in other places for shielding leaking neutrons.

Figure 4:
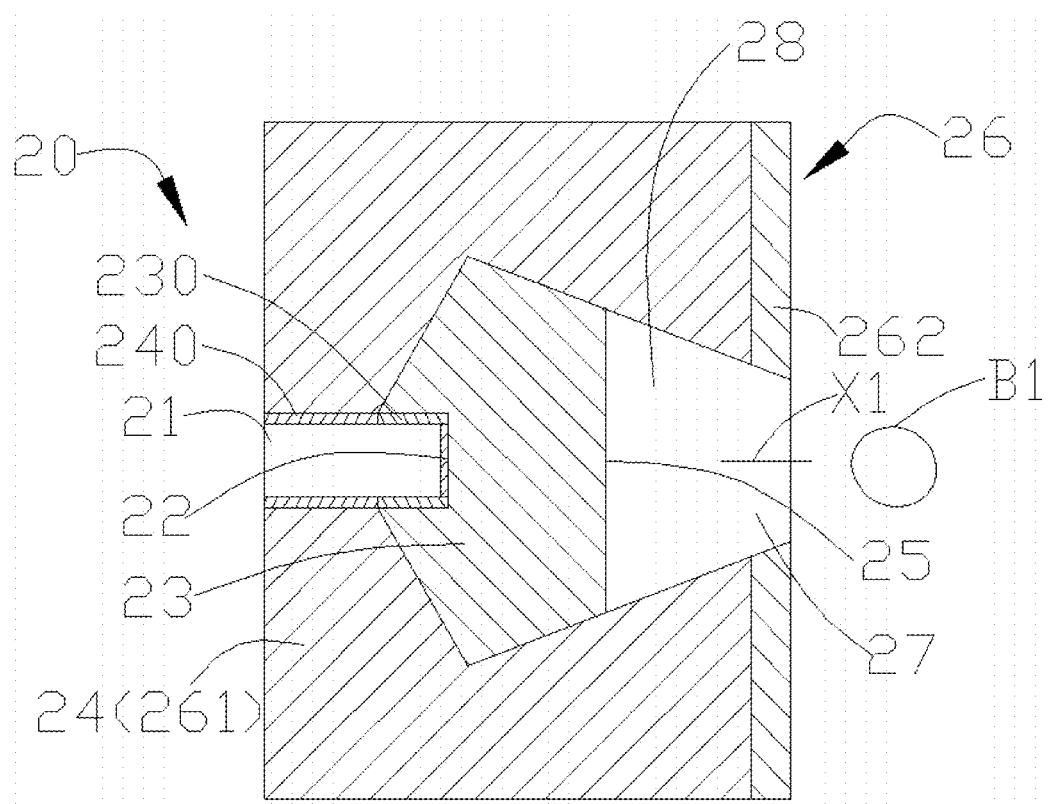
FIG. 4 is a schematic view of the beam shaping assembly for neutron capture therapy in the second embodiment of the present disclosure, wherein the outer surface of the moderator includes the first tapered section and a second tapered section adjoining to the first tapered section, and a tapering direction of the first tapered section is opposite to a tapering direction of the second tapered section, and the gap channel in the first embodiment is filled with materials of the moderator.
Figure 5:
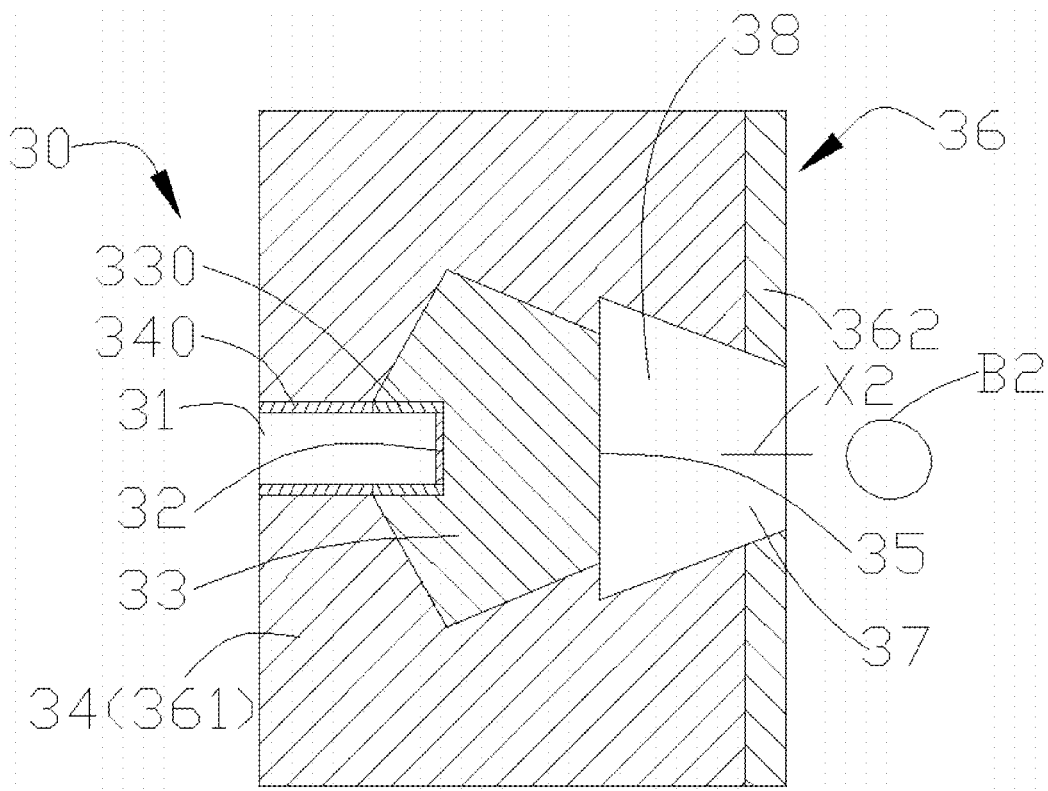
FIG. 5 is a schematic view of the beam shaping assembly for neutron capture therapy in the third embodiment of the present disclosure, wherein the outer surface of the moderator includes the first tapered section and a second tapered section adjoining to the first tapered section, and a tapering direction of the first tapered section is opposite to a tapering direction of the second tapered section, and the gap channel in the first embodiment is filled with materials of the reflector.

For comparing difference between the beam shaping assemblies with and without the gap channel, referring to FIGS. 4 and 5, the gap channel filled with the moderator in the second embodiment and the one filled with the reflector in the third embodiment are shown. Referring to FIG. 4 first, the beam shaping assembly 20 comprises a beam inlet 21, a target 22, a moderator 23 adjoining to the target 22, a reflector 24 surrounding the moderator 23, a thermal neutron absorber 25 adjacent to the moderator 23, a radiation shield 26 and a beam outlet 27, wherein the radiation shield 26 is set in the beam shaping assembly 20. The target 22 has nuclear reaction with an incident photon beam from the beam inlet 21 to produce neutrons, the neutrons form a neutron beam, the neutron beam defines a main axis X1, the neutrons are moderated by the moderator 23 to epithermal neutron energies, and the reflector 24 leads the neutrons deviated from the main axis X1 back to enhance the epithermal neutron beam intensity. The moderator 23 includes a recess 230 for receiving the target 22 and at least a part of the beam inlet 21. The reflector 24 includes a recess 240 for receiving the other part of the beam inlet 21. An outer surface of the moderator 23 includes the first tapered section and a second tapered section adjoining to the first tapered section, and a tapering direction of the first tapered section is opposite to a tapering direction of the second tapered section as shown in FIG. 4, the left side of the out surface of the moderator 23 is shaped in a first tapered section tapering gradually towards the left side, the right side of the out surface of the moderator 23 is shaped in a second tapered section tapering gradually towards the right side, and the two tapered sections connect to each other. The thermal neutron absorber 25 is used for absorbing thermal neutrons so as to avoid overdosing in superficial normal tissue during therapy; the radiation shield 26 is used for shielding leaking neutrons and photons so as to reduce dose of the normal tissue not exposed to irradiation.

Preferably, the target 22, the moderator 23, the reflector 24, the thermal neutron absorber 25 and the radiation shield 26 in the second embodiment may be same as those in the first embodiment, wherein the radiation shield 26 comprises a photon shield 261 made of lead (Pb) and a neutron shield 262 made of polyethylene (PE), and the neutron shield 262 may be arranged at the beam outlet 27. An air passage 28 is placed between the thermal neutron absorber 25 and the beam outlet 27. A prosthesis B1 is arranged at a position about 1 cm away from the beam outlet 27.

Referring to FIG. 5, the beam shaping assembly 30 comprises a beam inlet 31, a target 32, a moderator 33 adjoining to the target 32, a reflector 34 surrounding the moderator 33, a thermal neutron absorber 35 adjoining to the moderator 33, a radiation shield 36 and a beam outlet 37, wherein the radiation shield 36 is set in the beam shaping assembly 30. The target 32 has nuclear reaction with an incident photon beam from the beam inlet 31 to produce neutrons, the neutrons form a neutron beam, the neutron beam defines a main axis X2, the neutrons are moderated by the moderator 33 to epithermal neutron energies, and the reflector 34 leads the neutrons deviated from the main axis X2 back to enhance the epithermal neutron beam intensity. The moderator 33 includes a recess 330 for receiving the target 32 and at least a part of the beam inlet 31. The reflector 34 includes a recess 340 for receiving the other part of the beam inlet 31. An outer surface of the moderator 33 includes the first tapered section and a second tapered section adjoining to the first tapered section, and a tapering direction of the first tapered section is opposite to a tapering direction of the second tapered section as shown in FIG. 5, the left side of the out surface of the moderator 33 is shaped in a first tapered section tapering gradually towards the left side, the right side of the out surface of the moderator 33 is shaped in a second tapered section tapering gradually towards the right side, and the two tapered sections connect to each other. The thermal neutron absorber 35 is used for absorbing thermal neutrons so as to avoid overdosing in superficial normal tissue during therapy; the radiation shield 36 is used for shielding leaking neutrons and photons so as to reduce dose of the normal tissue not exposed to irradiation.

Preferably, the target 32, the moderator 33, the reflector 34, the thermal neutron absorber 35 and the radiation shield 36 in the third embodiment may be same as those in the first embodiment, wherein the radiation shield 36 comprises a photon shield 361 made of lead (Pb) and a neutron shield 362 made of polyethylene (PE), and the neutron shield 362 may be arranged at the beam outlet 37. An air passage 38 is placed between the thermal neutron absorber 35 and the beam outlet 37. A prosthesis B2 is arranged at a position about 1 cm away from the beam outlet 37.

The followings are analog computation of the three embodiments by MCNP software (a common-use software package developed by LosAlamos National Laboratory of the United States for computing neutrons, photons, charged particles or transporting coupled neutrons/photons/charged particles in 3D complicated geometric structures).

Among them, Table 1 as follow shows performances of air beam quality factors in the three different embodiments (each item in the table is calculated in the same unit above, so not repeat here and similarly hereinafter):

TABLE 1

Air Beam Quality Factors

| Air beam quality factors | Moderator-filled gap channel | Reflector-filled gap channel | Gap channel |
|---|---|---|---|
| Epithermal neutron flux | 1.35E+09 | 1.38E+09 | 1.42E+09 |
| Fast neutron contamination | 2.35E−13 | 2.58E−13 | 2.83E−13 |
| Photon contamination | 1.22E−13 | 8.92E−14 | 8.02E−14 |
| Thermal to epithermal neutron flux ratio | 0.03 | 0.02 | 0.02 |
| Epithermal neutron current to flux ratio | 0.64 | 0.64 | 0.64 |

Table 2 shows dose performance in the three embodiments:

TABLE 2

Dose Performance

| Dose Performance | Moderator-filled gap channel | Reflector-filled gap channel | Gap channel |
|---|---|---|---|
| Advantage depth | 10.9 | 10.9 | 11.0 |
| Advantage depth dose rate | 4.47 | 4.60 | 4.78 |
| Advantage rate | 5.66 | 5.69 | 5.68 |

Table 3 shows analog numerals of parameters for evaluating neutron beam dose in the three embodiments:

TABLE 3

Parameters for Evaluating Neutron Beam Dose

| Parameters | Moderator-filled gap channel | Reflector-filled gap channel | Gap channel |
|---|---|---|---|
| Irradiation time | 25.3 | 24.8 | 23.9 |
| 30.0RBE-Gy treatable depth | 7.7 | 7.7 | 7.7 |
| Maximum tumor dose | 68.5 | 69.1 | 68.8 |
| Maximum dose of normal brain tissue | 11.3 | 11.4 | 11.4 |
| Maximum skin dose | 11.0 | 11.0 | 11.0 |

Note: it is observed from the three tables that the beam shaping assembly with the gap channel between the moderator and the reflector may supply neutron beams having best therapeutic effect.

Figure 6:
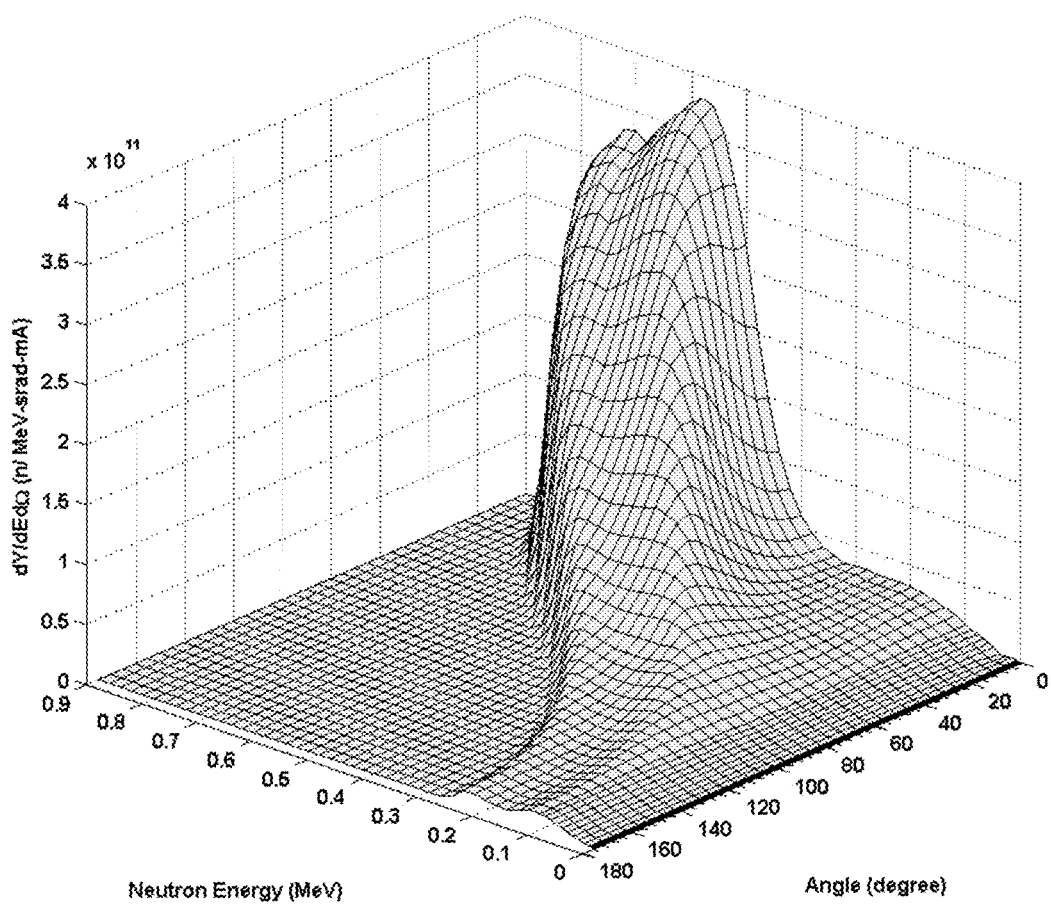
FIG. 6 is a double-differential graph of neutron yield from neutron energy and neutron angle.

Neutrons produced from the lithium target feature higher forward average energy. As shown in FIG. 6, the average neutron energy is about 478 keV at a neutron scattering angle between 0° and 30° of and is only about 290 keV between 30° and 180°. If forwardly travelling neutrons collide much with the moderator by changing the geometric shape of the beam shaping assembly, lateral neutrons may easily get to the beam outlet via less collision, so theoretically, neutron moderation may be best optimized and the epithermal neutron flux may be improved effectively. Now from geometric shapes of the beam shaping assembly we may evaluate influences on the epithermal neutron flux from different geometric shapes of the beam shaping assembly.

Figure 7:
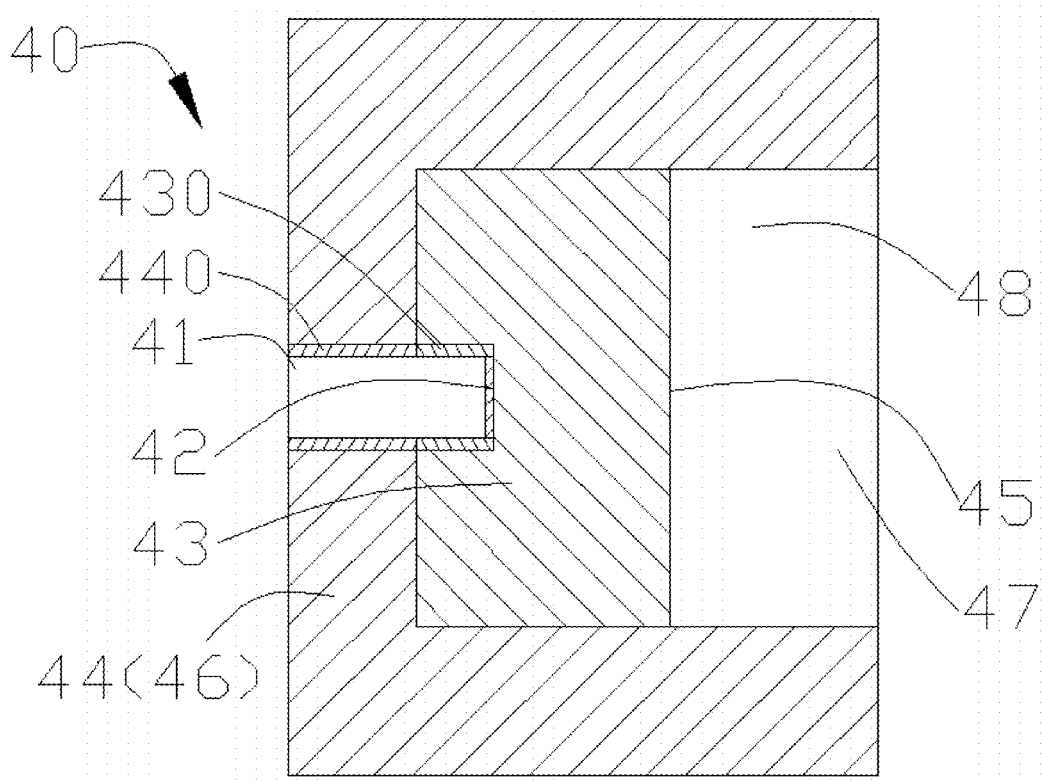
FIG. 7 is a schematic view of the beam shaping assembly for neutron capture therapy in the fourth embodiment of the present disclosure, wherein the moderator is cylindrical.

FIG. 7 is a view of a geometric shape of the beam shaping assembly in the fourth embodiment. The beam shaping assembly 40 comprises a beam inlet 41, a target 42, a moderator 43 adjoining to the target 42, a reflector 44 surrounding the moderator 43, a thermal neutron absorber 45 adjoining to the moderator 43, a radiation shield 46 and a beam outlet 47, wherein the radiation shield 46 is set in the bean shaping assembly 40. The target 42 has nuclear reaction with an incident photon beam from the beam inlet 41 to produce neutrons, the neutrons are moderated by the moderator 43 to epithermal neutron energies, and the reflector 44 leads the deviated neutrons back to enhance the epithermal neutron beam intensity. The moderator 43 includes a recess 430 for receiving the target 42 and at least a part of the beam inlet 41. The reflector 44 includes a recess 440 for receiving the other part of the beam inlet 41. An out surface of the moderator 43 is columnar, preferably, cylindrical. The thermal neutron absorber 45 is used for absorbing thermal neutrons so as to avoid overdosing in superficial normal tissue during therapy; the radiation shield 46 is used for shielding leaking neutrons and photons so as to reduce dose of the normal tissue not exposed to irradiation, and an air passage 48 is placed between the thermal neutron absorber 45 and the beam outlet 47.

Figure 8:
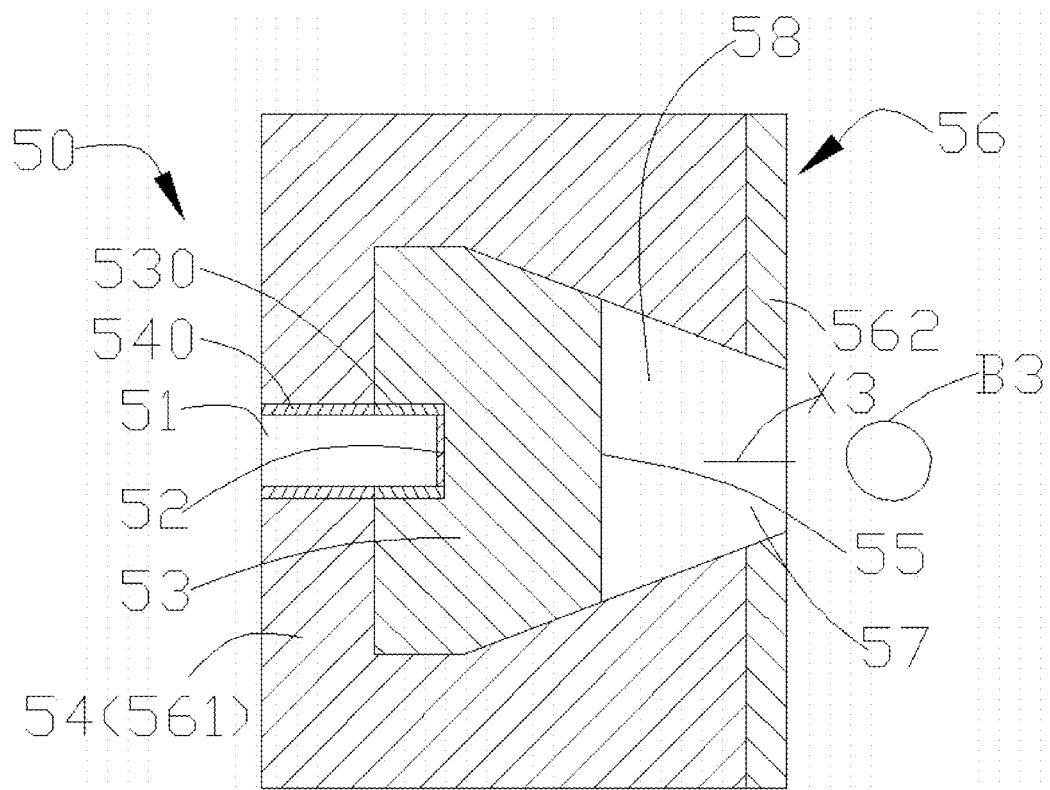
FIG. 8 is a schematic view of the beam shaping assembly for neutron capture therapy in the fifth embodiment of the present disclosure, wherein the outer surface of the moderator includes a cylindrical section and the first tapered section adjoining to the cylindrical section.

FIG. 8 is a view of a geometric shape of the beam shaping assembly in the fifth embodiment. The beam shaping assembly 50 comprises a beam inlet 51, a target 52, a moderator 53 adjoining to the target 52, a reflector 54 surrounding the moderator 53, a thermal neutron absorber 55 adjoining to the moderator 53, a radiation shield 56 and a beam outlet 57, wherein the radiation shield 56 is set in the beam shaping assembly 50. The target 52 has nuclear reaction with an incident photon beam from the beam inlet 51 to produce neutrons, the neutrons form a neutron beam, the neutron beam defines a main axis X3, the neutrons are moderated by the moderator 53 to epithermal neutron energies, and the reflector 54 leads the neutrons deviated from the main axis X3 back to enhance the epithermal neutron beam intensity. The moderator 53 includes a recess 530 for receiving the target 52 and at least a part of the beam inlet 51. The reflector 54 includes a recess 540 for receiving the other part of the beam inlet 51. An out surface of the moderator 53 includes a cylindrical section and a tapered section adjoining to the cylindrical section, the left side of the out surface of the moderator 53 is shaped in a cylinder, the right side of the out surface of the moderator 53 is shaped in a cone tapering gradually from the right side, and the cylinder and the cone are adjacent to each other. The thermal neutron absorber 55 is used for absorbing thermal neutrons so as to avoid overdosing in superficial normal tissue during therapy; the radiation shield 56 is used for shielding leaking neutrons and photons so as to reduce dose of the normal tissue not exposed to irradiation.

Preferably, the target 52, the moderator 53, the reflector 54, the thermal neutron absorber 55 and the radiation shield 56 in the fifth embodiment may be same as those in the first embodiment, wherein the radiation shield 56 comprises a photon shield 561 made of lead (Pb) and a neutron shield 562 made of polyethylene (PE), and the neutron shield 562 may be arranged at the beam outlet 57. An air passage 58 is placed between the thermal neutron absorber 55 and the beam outlet 57. A prosthesis B3 is arranged at a position about 1 cm away from the beam outlet 57.

In the following, results of analog computation of the moderator with an out surface including two opposite tapered sections in the second embodiment, the cylindrical moderator in the fourth embodiment and the moderator with an out surface including a cylindrical section and a tapered section adjoining to the cylindrical section in the fifth embodiment by MCNP are shown.

Among them, Table 4 shows air beam quality factors in these three embodiments:

TABLE 4

Air Beam Quality Factors

| Air beam quality factors | Cylindrical section | A cylindrical section and a tapered section | Two opposite tapered sections |
|---|---|---|---|
| Epithermal neutron flux | 7.14E+08 | 1.29E+09 | 1.35E+09 |
| Fast neutron contamination | 2.67E-13 | 2.40E-13 | 2.35E-13 |

TABLE 4-continued

Air Beam Quality Factors

| Air beam quality factors | Cylindrical section | A cylindrical section and a tapered section | Two opposite tapered sections |
|---|---|---|---|
| Photon contamination | 1.72E−13 | 1.42E−13 | 1.22E−13 |
| Thermal to epithermal neutron flux ratio | 0.04 | 0.03 | 0.03 |
| Epithermal neutron current to flux ratio | 0.69 | 0.64 | 0.64 |

Table 5 shows dose performance in these three embodiments:

TABLE 5

Dose Performance

| Dose Performance | Cylindrical section | A cylindrical section and a tapered section | Two opposite tapered sections |
|---|---|---|---|
| Advantage depth | 11.8 | 10.9 | 10.9 |
| Advantage depth dose rate | 2.95 | 4.28 | 4.47 |
| Advantage rate | 5.52 | 5.66 | 5.66 |

Table 6 shows analog numerals of parameters for evaluating neutron beam dose in these three embodiments:

TABLE 6

Parameters for Evaluating Neutron Beam Dose

| Parameters | Cylindrical section | A cylindrical section and a tapered section | Two opposite tapered sections |
|---|---|---|---|
| Irradiation time (10 mA) | 40.7 | 26.1 | 25.3 |
| 30.0RBE-Gy treatable depth | 8.4 | 7.6 | 7.7 |
| Maximum tumor dose | 70.9 | 67.4 | 68.5 |
| Maximum dose of normal brain tissue | 12.0 | 11.2 | 11.3 |
| Maximum skin dose | 11.0 | 11.0 | 11.0 |

Note: it is observed from these three tables that the out surface of the moderator may include at least one tapered section, and its neutron beams may achieve better therapeutic effect.

The term 'cylindrical' or 'cylindrical section' referred in the embodiment of the present disclosure is an element with the contour in a substantially unchanged trend from one side to the other side along the illustrated direction. One of contour lines may be a line segment, like a corresponding one of the cylinder, or may be a high-curvature arc approximate to the line segment, like a corresponding one of a sphere with high curvature. The integral surface of the contour may be continuously connected or not if the surface of the cylinder or the high-curvature sphere is provided with many protrusions and grooves.

The term 'tapered' or 'tapered section' referred in the embodiment of the present disclosure is an element with the contour in a tapering trend from one to the other side along the illustrated direction. One of contour lines may be a line segment, like a corresponding one of the cone, or may be an arc, like a corresponding one of the sphere, and the integral surface of the contour may be continuously connected or not if the surface of the cone shape or the spherical shape is provided with plenty of protrusions and grooves.

The above illustrates and describes basic principles, main features and advantages of the present disclosure. Those skilled in the art should appreciate that the above embodiments do not limit the present disclosure in any form. Technical solutions obtained by equivalent substitution or equivalent variations all fall within the scope of the present disclosure.

What is claimed is:

1. A beam shaping assembly for neutron capture therapy comprising:
   a beam inlet;
   a target, wherein the target has nuclear reaction with an incident proton beam from the beam inlet to produce neutrons, and wherein the neutrons form a neutron beam defining a main axis;
   a moderator adjoining to the target, wherein the neutrons are moderated by the moderator to epithermal neutron energies, the moderator includes a first side facing to the beam inlet and a second side facing away from the beam inlet;
   a reflector surrounding the moderator, wherein the reflector leads the neutrons deviated from the main axis back to enhance epithermal neutron beam intensity;
   a radiation shield arranged inside the beam shaping assembly, wherein the radiation shield is used for shielding leaking neutrons and photons so as to reduce dose of the normal tissue not exposed to irradiation; and
   a beam outlet,
   wherein all of the beam inlet, the moderator, the beam outlet and an incidence direction of the incident proton beam are extended along the main axis, an outer surface of the moderator includes a first single flat tapered section, defining an opening for the target and tapered in a first direction along the main axis and away from the beam outlet, the target is received into the opening defined by the first single flat tapered section, and the first side of the moderator contacts with the reflector.

2. The beam shaping assembly for neutron capture therapy according to claim 1, wherein the beam shaping assembly is further used for accelerator-based boron neutron capture therapy.

3. The beam shaping assembly for neutron capture therapy according to claim 2, wherein a proton beam is accelerated by means of an accelerator to overcome coulomb repulsion energy of a target atomic nucleus and generate nuclear reaction with the target to produce neutrons, and the target is made of a metal material.

4. The beam shaping assembly for neutron capture therapy according to claim 1, wherein an epithermal neutron energy range ranges from 0.5 eV to 40 keV, a thermal neutron energy range is below 0.5 eV, and a fast neutron energy range is above 40 keV, and the beam shaping assembly reduces the quantity of thermal neutrons and fast neutrons; and wherein the moderator is made of a material having a cross section for principally acting with fast neutrons but hardly acting with epithermal neutrons, the reflector is made of a material having a high neutron reflection ability.

5. The beam shaping assembly for neutron capture therapy according to claim 4, wherein the moderator is made of at least one of $D_2O$, $AlF_3$, $CaF_2$, $Li_2CO_3$, $MgF_2$ and $Al_2O_3$.

6. The beam shaping assembly for neutron capture therapy according to claim 1, wherein the beam shaping assembly further includes a thermal neutron absorber adjoining to the moderator, and wherein the thermal neutron absorber is used for absorbing thermal neutrons so as to avoid overdosing in superficial normal tissue during therapy.

7. The beam shaping assembly for neutron capture therapy according to claim 6, wherein the thermal neutron absorber is made of a material having a cross section for acting with thermal neutrons.

8. The beam shaping assembly for neutron capture therapy according to claim 6, wherein the reflector is made of at least one of Pb or Ni, and the thermal neutron absorber is made of $^6$Li, and wherein an air passage is arranged between the thermal neutron absorber and the beam outlet.

9. The beam shaping assembly for neutron capture therapy according to claim 1, wherein the radiation shield includes a photon shield and a neutron shield.

10. The beam shaping assembly for neutron capture therapy according to claim 1, wherein an outer surface of the moderator further includes a second single flat tapered section adjoining to the first single flat tapered section and tapered in a second direction toward the beam outlet.

11. The beam shaping assembly for neutron capture therapy according to claim 1, wherein the beam shaping assembly includes a gap channel arranged between the moderator and the reflector, and wherein the gap channel allows neutron beams to pass for enhancing epithermal neutron beam intensity.

12. A beam shaping assembly for neutron capture therapy comprising:
    a beam inlet;
    a target, wherein the target has nuclear reaction with an incident proton beam from the beam inlet to produce neutrons, and wherein the neutrons form a neutron beam defining a main axis;
    a moderator adjoining to the target, wherein the neutrons are moderated by the moderator to epithermal neutron energies, and wherein the moderator has a first trapezidal cross section facing to the beam inlet;
    a reflector surrounding the moderator, wherein the reflector leads the neutrons deviated from the main axis back to enhance epithermal neutron beam intensity;
    a radiation shield arranged inside the beam shaping assembly, wherein the radiation shield is used for shielding leaking neutrons and photons so as to reduce dose of the normal tissue not exposed to irradiation; and
    a beam outlet,
    wherein the target is received into the first trapezoidal cross section, and all of the beam inlet, the moderator, the beam outlet and an incidence direction of the incident proton beam are extended along the main axis.

13. The beam shaping assembly for neutron capture therapy according to claim 12, wherein the moderator has a second trapezidal cross section facing away from the beam inlet and adjoining to the first trapezidal cross section.

14. The beam shaping assembly for neutron capture therapy according to claim 12, wherein the beam shaping assembly includes a gap channel arranged between the moderator and the reflector and enclosed by the reflector, the moderator and the thermal neutron absorber, and wherein the gap channel allows neutron beams to pass for enhancing epithermal neutron beam intensity.

15. The beam shaping assembly for neutron capture therapy according to claim 12, wherein the moderator comprises a recess for receiving the target and at least a part of the beam inlet and the reflector comprises a recess for receiving the other part of the beam inlet.

16. A beam shaping assembly for neutron capture therapy comprising:
    a beam inlet;
    a target, wherein the target has nuclear reaction with an incident proton beam from the beam inlet to produce neutrons, and wherein the neutrons form a neutron beam defining a main axis;
    a moderator adjoining to the target, wherein the neutrons are moderated by the moderator to epithermal neutron energies, the moderator includes a first side facing to the beam inlet and a second side facing away from the beam inlet, and wherein the outer surface of the moderator includes a first trapezoidal cross section facing the beam inlet;
    a reflector surrounding the moderator, wherein the reflector leads the neutrons deviated from the main axis back to enhance epithermal neutron beam intensity;
    a radiation shield arranged inside the beam shaping assembly, wherein the radiation shield is used for shielding leaking neutrons and photons so as to reduce dose of the normal tissue not exposed to irradiation; and
    a beam outlet,
    wherein the target is received into the first trapezoidal cross section, all of the beam inlet, the moderator, the beam outlet and an incidence direction of the incident proton beam are extended along the main axis, a distance from the target to the beam outlet is closer than a distance from the first side to the beam outlet; and
    wherein the moderator comprises a recess for receiving the target and at least a part of the beam inlet and the reflector comprises a recess for receiving the other part of the beam inlet.

17. The beam shaping assembly for neutron capture therapy according to claim 16, wherein the first side is protruded from the target along a direction from the main axis to the beam inlet and the second side is protruded from the target along a direction from the main axis to the beam outlet.

* * * * *